United States Patent
Hesse et al.

(10) Patent No.: US 7,154,011 B2
(45) Date of Patent: Dec. 26, 2006

(54) METHOD FOR THE PRODUCTION OF 1,4-BUTANEDIOL

(75) Inventors: Michael Hesse, Worms (DE); Stephan Schlitter, Limburgerhof (DE); Holger Borchert, Offstein (DE); Markus Schubert, Ludwigshafen (DE); Markus Rösch, Oppenheim (DE); Nils Bottke, Mannheim (DE); Rolf-Hartmuth Fischer, Heidelberg (DE); Alexander Weck, Freinsheim (DE); Gunther Windecker, Ludwigshafen (DE); Gunnar Heydrich, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 183 days.

(21) Appl. No.: 10/517,263

(22) PCT Filed: Jun. 10, 2003

(86) PCT No.: PCT/EP03/06062

§ 371 (c)(1),
(2), (4) Date: Dec. 7, 2004

(87) PCT Pub. No.: WO03/104174

PCT Pub. Date: Dec. 18, 2003

(65) Prior Publication Data

US 2005/0182281 A1    Aug. 18, 2005

(30) Foreign Application Priority Data

Jun. 11, 2002 (DE) .................................. 102 25 926

(51) Int. Cl.
*C07C 29/149* (2006.01)
(52) U.S. Cl. ..................................................... 568/864
(58) Field of Classification Search ................. 568/864
See application file for complete search history.

(56) References Cited

U.S. PATENT DOCUMENTS

| | | | |
|---|---|---|---|
| 3,925,352 A | 12/1975 | Bojarska-Dahling et al. |
| 3,967,057 A | 6/1976 | Tsukamoto et al. |
| 4,001,282 A | 1/1977 | Miller et al. |
| 4,268,695 A | 5/1981 | Lange et al. |
| 4,301,077 A | 11/1981 | Pesa et al. |
| 4,652,685 A | 3/1987 | Cawse et al. |
| 4,797,382 A | 1/1989 | DeThomas et al. |
| 4,885,411 A | 12/1989 | DeThomas et al. |
| 4,940,805 A | 7/1990 | Fischer et al. |
| 4,965,378 A | 10/1990 | Budge et al. |
| 5,030,773 A | 7/1991 | Johnson et al. |
| 5,072,009 A | 12/1991 | Budge et al. |
| 5,122,495 A | 6/1992 | Taylor et al. |
| 5,149,836 A | 9/1992 | DeThomas et al. |
| 5,196,602 A | 3/1993 | Budge et al. |
| 5,395,990 A | 3/1995 | Scarlett |
| 5,406,004 A | 4/1995 | Eastland et al. |
| 5,536,849 A | 7/1996 | Bergfeld et al. |
| 6,008,375 A | 12/1999 | Bergfeld et al. |
| 6,075,153 A | 6/2000 | Bergfeld et al. |
| 6,297,389 B1 | 10/2001 | Castiglioni et al. |

FOREIGN PATENT DOCUMENTS

| | | |
|---|---|---|
| DE | 2 231 986 | 1/1974 |
| DE | 2 404 493 | 8/1974 |
| DE | 24 55 617 | 5/1976 |
| DE | 25 01 499 | 7/1976 |
| DE | 28 45 905 | 4/1980 |
| DE | 37 26 510 | 2/1989 |
| EP | 318 129 | 5/1989 |
| EP | 322 140 | 6/1989 |
| EP | 373 946 | 6/1990 |
| EP | 373 947 | 6/1990 |
| EP | 382 050 | 8/1990 |
| EP | 404 408 | 12/1990 |
| EP | 431 923 | 6/1991 |

(Continued)

OTHER PUBLICATIONS

Patent absts. of Japan 634 567.

(Continued)

*Primary Examiner*—Bernard Dentz
(74) *Attorney, Agent, or Firm*—Novak Druce & Quigg, LLP

(57) ABSTRACT

The present invention relates to a process for preparing optionally alkyl-substituted 1,4-butanediol by two-stage catalytic hydrogenation in the gas phase of $C_4$-dicarboxylic acids and/or of derivatives thereof having the following steps:

a) introducing a gas stream of a $C_4$-dicarboxylic acid or of a derivative thereof at from 200 to 300° C. and from 10 to 100 bar into a first reactor or into a first reaction zone of a reactor and catalytically hydrogenating it in the gas phase to a product which contains mainly optionally alkyl-substituted γ-butyrolactone;

b) introducing the product stream obtained in this way into a second reactor or into a second reaction zone of a reactor at a temperature of from 140° C. to 260° C. and catalytically hydrogenating it in the gas phase to optionally alkyl-substituted 1,4-butanediol;

steps a) and b) being carried out at the same pressure;

c) removing the desired product from intermediates, by-products and any unconverted reactants;

d) optionally recycling unconverted intermediates into one or both hydrogenation stages, said hydrogenation stages each using a catalyst which comprises $\leq 95\%$ by weight, preferably from 5 to 95% by weight, in particular from 10 to 80% by weight, of CuO, and $\geq 5\%$ by weight, preferably from 5 to 95% by weight, in particular from 20 to 90% by weight, of an oxidic support, and the product mixture removed from the first hydrogenation stage being introduced without further purification into the second hydrogenation stage.

28 Claims, No Drawings

FOREIGN PATENT DOCUMENTS

| | | |
|---|---|---|
| EP | 638 565 | 2/1995 |
| GB | 1059598 | 2/1967 |
| GB | 1168220 | 10/1969 |
| GB | 1 230 276 | 4/1971 |
| GB | 1 344 557 | 1/1974 |
| GB | 1 512 751 | 1/1975 |
| JP | 44-5366 | 3/1944 |
| JP | 47-40770 | 10/1972 |
| JP | 49-24906 | 3/1974 |
| JP | 49-87610 | 8/1974 |
| WO | 82/03854 | 11/1982 |
| WO | 91/16132 | 10/1991 |
| WO | 95/22539 | 8/1995 |
| WO | 95/35136 | 12/1995 |
| WO | 97/24346 | 7/1997 |
| WO | 97/43234 | 11/1997 |
| WO | 99/35113 | 7/1999 |
| WO | 99/35114 | 7/1999 |
| WO | 99/35139 | 7/1999 |
| WO | 99/38856 | 8/1999 |
| WO | 99/52845 | 10/1999 |

OTHER PUBLICATIONS

Journal of Catalysis 150, 177-185 (1994) Messori et al.
Patent Absts.Japan; 01-121228.
Patent Absts. Japan; 02-233627.
Patent Absts. Japan; 02-233630.
Patent Absts. Japan; 02-233632.
Patent Absts. Japan; 02-233631.
Substituted Lactones and their Transformation . . . . Dashunin et al., 1003-1006.
Abst. EP 382-050.
CN1113831 Derwent Abst.
CN1116615 Derwent Abst.
CN1138018 Derwent Abst.
CN 1047-328 Derwent Abst.
CN1137944 Derwent Abst.
CN1182639 Derwent Abst.
CN1182732 Derwent Abst.

METHOD FOR THE PRODUCTION OF 1,4-BUTANEDIOL

This application is a 371 of PCT/EP03/06062 filed Jun. 10, 2003.

The present invention relates to a process for preparing optionally alkyl-substituted butanediol by catalytic gas-phase hydrogenation of substrates which are selected from the group consisting of derivatives of maleic acid and succinic acid and also these acids themselves. For the purposes of the present invention, derivatives are anhydrides which, like the acids, may have one or more alkyl substituents.

The hydrogenation of MA which is known per se leads via the intermediate succinic anhydride (SA) initially to γ-butyrolactone (GBL). Further hydrogenation then leads to tetrahydrofuran (THF), n-butanol (BuOH) and/or n-butane. GBL and BDO are in an equilibrium which can be shifted by suitable measures substantially to the side of butanediol. However, butanediol can react just as easily as GBL by overhydrogenation to give butanol and butane; cyclization of butanediol gives THF. These products cannot be converted back to BDO or GBL. When BDO is the desired product, the formation of THF in particular has to be avoided.

The gas phase hydrogenation of purified maleic anhydride (MA) to butyrolactone (GBL) and the conversion of purified GBL to BDO are two reactions which have been known for many years. To carry out these two catalytic reactions, the literature describes numerous catalyst systems. Depending on the composition of the catalysts and the reaction parameters chosen, such catalysts give different product distributions. Processes for direct preparation of butanediol starting from MA are likewise already known.

When GBL and BDO which have alkyl substituents are to be prepared, there is the possibility of using the corresponding alkyl-substituted species of the abovementioned reactants.

The catalysts used for hydrogenating MA to one of the abovementioned products, in particular in older processes, frequently contain chromium. This is reflected by the patent literature where a large number of patents and patent applications disclose the use of chromium catalysts for the hydrogenation reaction, although the hydrogenation in most cases is restricted to MA as the reactant.

The documents hereinbelow describe the use of chromium catalysts for hydrogenating MA.

EP 0 322 140-A1 discloses a continuous process for preparing tetrahydrofuran (THF) and for coproduction of THF and GBL by gas phase hydrogenation of MA and SA. The claimed catalyst contains copper, zinc and aluminum and a further element of groups IIA, IIIA, VA, VIII, IIIB to VIIB, the lanthanide and actinide series, and also Ag and Au. At 40 bar, these catalyst systems achieve THF yields of 90–95% starting from pure MA, and at a pressure of about 20 bar mixtures of GBL and THF can be obtained.

In U.S. Pat. No. 4,965,378 and U.S. Pat. No. 5,072,009, a similar catalyst is used which may, however, additionally contain Si, Ge, Sn and Pb. The use of such catalysts results in high quantities of THF (from 95% to 31.4%) which cannot be converted to butyrolactone or butanediol.

EP-A 0 404 408 discloses an MA hydrogenation catalyst whose catalytically active material corresponds substantially to the material of U.S. Pat. No. 5,072,009. It is used fixed on a support as a coated catalyst. In the examples, exclusively chromium catalysts are used. High GBL yields can be realized at a pressure of 2 bar, but when a higher pressure is used the THF yield increases while the GBL yield decreases.

U.S. Pat. No. 5,149,836 discloses a multistage gas phase process for preparing GBL and THF with variable product selectivities by, in a first stage, passing a mixture of pure MA and hydrogen over a catalyst which comprises copper, zinc and aluminum. This crude reaction effluent is then passed over a chromium catalyst to prepare THF.

WO 99/38856 discloses a catalyst comprising only copper and chromium which allows GBL selectivities of from 92 to 96 mol % to be obtained in straight paths starting from pure MA.

EP-A 638 565 discloses a copper-, chromium- and silicon-containing catalyst which has a composition in one example of about 78% of CuO, 20% of $Cr_2O_3$ and 2% of $SiO_2$. Using pure MA and nitrogen-hydrogen mixtures, GBL yields of 98% could be obtianed.

The documents hereinbelow disclose the use of chromium-free catalysts for hydrogenating MA.

GB-A 1 168 220 discloses a gas phase process for preparing GBL by hydrogenating MA or SA over a binary copper-zinc catalyst to GBL. In all examples, operation is effected at atmospheric pressure and GBL yields of 94 mol % could be obtained starting from pure MA.

German laid-open specification 2 404 493 likewise discloses a process for preparing GBL by catalytically hydrogenating mixtures of MA, SA, maleic acid, succinic acid and water over metallic catalysts, and as well as copper chromite catalysts, copper-zinc and copper-zinc-aluminum precipitated catalysts are also used.

WO 91/16132 discloses the hydrogenation of MA to GBL using a catalyst comprising CuO, ZnO and $Al_2O_3$ which is reduced at from 150° C. to 350° C. and activated at 400° C. The activation is intended to increase the on-stream time of the catalyst system.

A catalyst comprising CuO and ZnO is disclosed by U.S. Pat. No. 6,297,389. After activation, this converts pure MSA to GBL in yields of from 92 to 96% and in straight paths starting from pure MA.

WO 95/22539 discloses a process for preparing GBL by catalytically hydrogenating MA and/or SA over a catalyst which consists of copper, zinc and zirconium. Starting from pure MA, GBL yields of up to 99% are obtained.

WO 99/35136 discloses a two-stage process for preparing GBL and THF by hydrogenating MA in a first stage using a copper catalyst and passing this reaction effluent over an acidic silicon-aluminum catalyst.

WO 97/24346 describes a copper oxide-aluminum oxide catalyst which hydrogenates MA to GBL in yields of 92 mol %.

The conversion of GBL to BDO is also a reaction which has been known for some time. The documents mentioned hereinbelow disclose this reaction using chromium catalysts.

DE 1 277 233 discloses a process for preparing mixtures of different alcohols by hydrogenating lactones using hydrogen. The catalysts used are copper chromite admixed with barium on an inactive aluminum oxide support.

GB-A 1 230 276 discloses a process for preparing BDO from GBL over a copper oxide-chromium oxide catalyst at a temperature of from 180° C. to 230° C.

According to DE-A 2 231 986, copper chromite catalysts which are doped using potassium, sodium, rubidium, aluminum, titanium, iron, cobalt or nickel increase the on-stream time of the catalysts.

According to DE-A 2 501 499, BDO is prepared using a mixture of dioxane, GBL, water and carboxylic acids. The reaction described takes place at high pressure (170 bar) in the liquid phase, preferably using the solvent dioxane, and copper-chromium oxide catalysts are likewise used.

Copper chromite catalysts are doped according to J01121-228-A using Pd in order to achieve a higher conversion.

Further copper chromite catalysts are described by Dasunin, Maeva, Z. Org. chim. 1 (1965), No. 6, p 996–1000; JA 5366/69; JA 7240770; J49024-906; J49087-610; and the examples concern the liquid phase conversion of pure GBL to BDO.

The gas phase hydrogenation of pure GBL to butanediol over copper chromite catalysts is described in U.S. Pat. No. 4,652,685. At a pressure of 41 bar and a conversion of 60–68%, a BDO selectivity of 92–97% could be achieved.

U.S. Pat. No. 5,406,004 and U.S. Pat. No. 5,395,990 disclose processes for preparing mixtures of alcohols and diols by hydrogenating pure GBL over copper catalysts. A hydrogenation zone filled with copper catalyst is charged with hydrogenation feed and hydrogen at a temperature of from 150 to 350° C. and pressures of from 10.3 bar to 138 bar, and a product composed of alcohols and diols is isolated. In the examples, a series of catalysts containing copper, zinc and chromium is described.

Finally, the documents cited hereinbelow disclose the use of chromium-free copper catalysts for hydrogenating GBL to BDO.

A catalyst consisting of CuO and ZnO is described in WO 82/03854. In the gas phase at a pressure of 28.5 bar and a temperature of 217° C., this achieves a BDO selectivity of 98.4%. However, the conversion of pure GBL is unsatisfactorily low.

Deposited copper catalysts doped with palladium and potassium are described in U.S. Pat. No. 4,797,382; U.S. Pat. No. 4,885,411 and EP-A 0 318 129. They are suitable for converting GBL to butanediol.

The use of a mixture of GBL and water as the feed stream in combination with a copper oxide-zinc oxide catalyst is described in U.S. Pat. No. 5,030,773 A. This discloses that the activity of such catalysts increases when from 1 to 6% of water is admixed into the pure GBL stream and this mixture is hydrogenated in the gas phase. When pure GBL is used in this reaction, extra water has to be admixed and then has to be removed again. If GBL were to be used which resulted from hydrogenation of MA, 17% of water would be present in the feed.

Accordingly, at least 11% of water would have to be removed before hydrogenation to BDO.

JP 0 634 567-A describes a catalyst comprising copper, iron and aluminum which is suitable for hydrogenating pure GBL to BDO at high pressure (250 bar).

A process for preparing BDO starting from maleic esters is cited in WO 99/35113. Hydrogenation is effected in three successive stages. Starting from maleic esters, succinic ester is prepared over a noble metal catalyst and is then converted in a second stage to GBL and THF. GBL is removed and converted to BDO in a third stage at elevated pressure.

WO 99/35114 describes a process for preparing BDO by liquid phase hydrogenation of GBL, succinic esters or mixtures of the two at pressures of from 60 bar to 100 bar and temperatures of from 180° C. to 250° C. The catalyst used is a copper oxide-zinc oxide catalyst.

A further gas phase variant of hydrogenation of GBL to BDO is disclosed by WO 99/52845 and uses a copper oxide-zinc oxide catalyst. In addition to the customary reaction feed, carbon monoxide is admixed with the hydrogen in order to coproduce methanol.

EP-A 0 382 050 concerns the hydrogenation of pure GBL over a catalyst comprising cobalt oxide, copper oxide, manganese oxide and molybdenum oxide.

Direct preparation of BDO starting from MA is also known. The documents cited hereinbelow describe this reaction using chromium catalysts.

DE 2 845 905 describes a continuous process for preparing butanediol starting from maleic anhydride. MA dissolved in monohydric aliphatic alcohols is reacted with hydrogen at pressures of 250 bar and 350 bar over copper chromite catalysts.

A process for coproducing BDO and THF starting from MA over copper-, chromium- and manganese-containing catalysts is disclosed by EP-A 0 373 947. Mixtures of MA and GBL, mixtures of MA and 1,4-dioxane and pure MA are used. In all cases, mixtures of THF and BDO are obtained. A disadvantage of this process is the high yields of tetrahydrofuran.

The documents CN-A 1 113 831-A, CN-A 1 116 615-A, CN-A 1 138 018-A and CN-A 1 047 328 disclose chromium catalysts. CN 1 137 944 A uses a copper, chromium, manganese, barium and titanium catalyst.

According to the disclosure of CN-A 1 182 639, a copper, chromium, zinc and titanium catalyst can be utilized for hydrogenating mixtures of GBL and MA.

CN-A 1 182 732 describes a process for preparing BDO by gas phase hydrogenation of MA over copper and chromium catalysts at from 200 to 250° C. and a pressure of from 30 to 70 bar. MA is hydrogenated dissolved in a suitable solvent.

The documents cited hereinbelow disclose finally the direct hydrogenation of MA to BDO using chromium-free catalysts.

For instance, DE-A 2 455 617 describes a three-stage process for preparing BDO. In a first stage, solutions of MA in GBL are hydrogenated to SA in GBL over a nickel catalyst. In a second stage at high pressure (80–200 bar) and at relatively high temperature, this solution of SA and GBL is hydrogenated to GBL in the liquid phase, then water, succinic anhydride and succinic acid are removed from GBL and the pure GBL is partially recycled and converted to butanediol in a third process stage over a copper-zinc oxide catalyst in the liquid phase at high pressure.

In U.S. Pat. No. 4,301,077, a ruthenium catalyst is used to hydrogenate MA to BDO.

DE-A 3 726 510 discloses the use of a catalyst comprising copper, cobalt and phosphorus for direct hydrogenation of MA.

In J0 2025-434-A, a pure copper oxide-zinc oxide catalyst is used. According to the examples, pure MA may be converted at a pressure of 40 bar. However, the yield of butanediol is only 53.3 mol %, and a secondary yield of 40.2 mol % of GBL is found.

EP-A 373 946 discloses a process by which gas phase MA is converted directly to BDO using a rhenium-doped copper oxide-zinc oxide catalyst.

The coproduction of BDO and THF is provided by patent applications J0 2233-627-A (using a copper-zinc-aluminum catalyst), J0 2233-630-A (using a copper-chromium catalyst comprising manganese, barium and silicon), and J0 2233-631-A (using a catalyst comprising copper and aluminum). The use of these catalysts results in the production of large quantities of THF as well as BDO from MA as well as BDO.

A catalyst comprising copper, manganese and potassium is described in J0-A 2233-632.

EP-A 431 923 describes a two-stage process for preparing BDO and THF by preparing GBL in a first stage by liquid phase hydrogenation of MA and converting it in a second stage to butanediol by gas phase reaction over a catalyst comprising copper and silicon.

U.S. Pat. No. 5,196,602 discloses a process for preparing butanediol by hydrogenating MA or maleic acid using hydrogen in a two-stage process. In a first stage, MA is hydrogenated to SA and/or GBL which is then converted to BDO in a second stage in the presence of an Ru-containing catalyst.

The technologies on which the above-cited documents are based utilize prepurified MA, which, after its preparation, has generally been freed of impurities by distillation, as a reactant in the hydrogenation reactions MA is prepared by partial oxidation of certain hydrocarbons including benzene, butene mixtures and also n-butane, and preference is given to using the latter. The crude product of the oxidation, in addition to the desired MA, comprises in particular by-products such as water, carbon monoxide, carbon dioxide, unconverted starting hydrocarbon and also acetic and acrylic acid, and these by-products are independent of the hydrocarbons used in the oxidation. Normally, the by-products are removed by complicated processes, for example by distillation, as mentioned above. The purification is necessary in particular because the catalysts used in the hydrogenation processes are generally sensitive to such impurities. The deactivation of the catalysts is a problem even when purified MA is used, since fouling by polymerization products thereof means that the catalyst generally has to be regenerated at relatively short intervals which are often about 100 hours. The tendency to deactivation is increased further when polymerizable impurities, for example acrylic acid, are present. This fact is known to those skilled in the art and is also described, for example, in patent applications EP-A 322 140, WO 91/16132 and DE-A 240 44 93.

Hitherto, only a single document in the prior art discloses the hydrogenation of only coarsely pre-purified MA. WO 97/43234 discloses the absorption of maleic anhydride from maleic anhydride-containing gas streams which stem from the oxidation of hydrocarbons using absorbents which boil at least 30° C. higher, stripping the maleic anhydride from these absorbents with the aid of hydrogen and hydrogenating the maleic anhydride containing hydrogen stream in the gas phase over a heterogeneous catalyst. This gives mainly BDO, as well as small quantities of GBL and THF. The hydrogenation is carried out at from about 150° C. to 300° C. and a pressure of from 5 bar to 100 bar in the gas phase. The catalysts used are promoted copper catalysts as described in Journal of Catalysis 150, pages 177 to 185 (1994). These are chromium catalysts of the Cu/Mn/Ba/Cr and Cu/Zn/Mg/Cr type. Accordingly, this application discloses the use of chromium catalysts for hydrogenating grades of MA which have the abovementioned impurities. However, the use of chromium catalysts is today avoided as far as possible owing to their toxicity.

Owing to their toxicity, novel technologies are moving more and more away from the use of chromium catalysts. Examples of chromium-free catalyst systems can be found in the documents WO 99/35139 (Cu—Zn oxide), WO 95/22539 (Cu—Zn—Zr) and also U.S. Pat. No. 5,122,495 (Cu—Zn—Al oxide).

In the field of MA hydrogenation to subsequent products, in particular GBL, THF and/or BDO, there is thus a virtually limitless prior art, and only a selection of the entire existing prior art has been cited above.

To summarize, it can be said that the technical problems occurring in preparing BDO by hydrogenating MA have been solved in that satisfactory yields and selectivities for BDO, i. e. only insignificant formation of THF, have been achieved. This has been achieved by different measures or the combination of different measures.

In general, BDO has been obtained by direct hydrogenation of pure GBL which has been obtained in turn by the hydrogenation of MA and subsequent costly and inconvenient purification. In every case, the reactant used was pure MA which only contains small quantities of impurities, since otherwise no satisfactory selectivity and catalyst on-stream time could be achieved. Chromium catalysts were used, in particular in the second stage, in order to achieve high BDO selectivity and the desired on-stream time. To avoid the use of chromium catalysts, there is the alternative of using noble metal catalysts which, in terms of yield, selectivity and also durability, are comparable with chromium catalysts, but are distinctly more costly.

The preferred procedure of the reaction in two separate stages also involves costly and inconvenient purification of the GBL after the first hydrogenation stage in order to achieve a long on-stream time of the catalysts, in particular with regard to the desired selectivity. Hitherto, the abovementioned WO 97/43234 discloses the only process which uses only coarsely prepurified MA as the reactant for preparing BDO by hydrogenation. The process is carried out in one stage, and so avoids the workup after the first hydrogenation stage. However, only chromium catalysts are suitable for this conversion.

It is an object of the present invention to provide a process for preparing BDO from MA which makes it possible to obtain BDO in good yields and has very low apparatus demands, while not requiring the use of pure MA or any intermediate purification of the first stage reaction products. The process shall further require no chromium catalysts, and preferably also no catalysts which comprise noble metals, and shall also have a high selectivity for BDO, and in particular deliver little THF.

We have found that this object is achieved by a process for preparing optionally alkyl-substituted 1,4-butanediol by two-stage catalytic hydrogenation in the gas phase of $C_4$-dicarboxylic acids and/or of derivatives thereof having the following steps:

a) introducing a gas stream of a $C_4$-dicarboxylic acid or of a derivative thereof at from 200 to 300° C. and from 10 to 100 bar into a first reactor or into a first reaction zone of a reactor and catalytically hydrogenating it in the gas phase to a product which contains mainly optionally alkyl-substituted γ-butyrolactone;

b) introducing the product stream obtained in this way into a second reactor or into a second reaction zone of a reactor at a temperature of from 140° C. to 260° C. and catalytically hydrogenating it in the gas phase to optionally alkyl-substituted 1,4-butanediol;

steps a) and b) being carried out at the same pressure;

c) removing the desired product from intermediates, by-products and any unconverted reactant;

d) optionally recycling unconverted intermediates into one or both hydrogenation stages, said hydrogenation stages each using a catalyst which comprises ≦95% by weight, preferably from 5 to 95% by weight, in particular from 10 to 80% by weight, of CuO, and ≧5% by weight, preferably from 5 to 95% by weight, in particular from 20 to 90% by weight, of an oxidic support, and the product mixture removed from the first hydrogenation stage being introduced without further purification into the second hydrogenation stage.

For the purposes of the present application, the "same pressure" in steps a) and b) means that the product stream leaving the first reactor or first reaction zone is neither compressed nor depressurized before it enters the second reactor or the second reaction zone. The reaction is generally carried out in a hydrogenation cycle using only one compressor. Certain pressure variations between the first and the second reactors or the first and the second reaction zones may occur owing to factors known to those skilled in the art which are generally caused by apparatus. The pressure variations may be up to a few bar. With the aid of the process according to the invention, the apparatus demands are substantially lowered compared to the prior art two-stage processes in which the second stage (reduction of GBL to BDO) is carried out at higher pressures than the first stage (reduction of MA to GBL). This results in cost-effective process operation.

The process according to the invention enables relatively high BDO selectivities to be achieved.

In order to be able to achieve the desired BDO selectivities, the maintenance of certain reaction parameters in both hydrogenation stages is necessary, and these parameters are cited hereinbelow.

For the purposes of the present application, "first reactor" refers hereinbelow to both "first reactor" and also, when the first and second hydrogenation stages are carried out in a reactor having more than one reaction zone, "first reaction zone". Equally, "second reactor" refers to both "second reactor" and also, when the first and second hydrogenation stages are carried out in a reactor having more than one reaction zone, "second reaction zone".

In the process according to the invention, reactants of differing purity may be used in the hydrogenation reaction. It will be appreciated that a reactant of high purity, in particular MA, may be used in the hydrogenation reaction. However, an advantage of the process according to the invention is further that the use of reactants, in particular MA, which is contaminated with the customary compounds resulting from the oxidation, i. e. benzene, butenes or n-butane, and also any further components, is also made possible. Accordingly, the hydrogenation process according to the invention in a further embodiment may comprise a preceding stage which comprises the preparation of the reactant to be hydrogenated by partial oxidation of a suitable hydrocarbon and also the removal of the reactant to be hydrogenated from the product stream obtained. Preference is given to carrying out only a coarse removal which requires no unnecessary effort and allows a quantity of impurities to remain in the reactant which was intolerable by the prior art processes.

In particular, this reactant to be hydrogenated is MA. Preference is given to using MA which stems from the partial oxidation of hydrocarbons. Useful hydrocarbons include benzene, $C_4$-olefins (for example n-butene, $C_4$-raffinate streams) or n-butane. Particular preference is given to using n-butane, since it is an inexpensive, economical starting material. Processes for the partial oxidation of n-butane are described, for example, in Ullmann's Encyclopedia of Industrial Chemistry, 6th Edition, Electronic Release, maleic and fumaric acids—maleic anhydride.

Preference is given to then taking up the reaction effluent obtained in this manner in a suitable organic solvent or solvent mixture which has a boiling point at atmospheric pressure which is at least 30° C. higher than that of MA.

This solvent (absorbent) is brought to a temperature in the range from 20 to 160° C., preferably from 30 to 80° C. The maleic anhydride-containing gas stream from the partial oxidation may be contacted with the solvent in various ways: (i) passing the gas stream into the solvent (for example via gas inlet nozzles or sparging rings), (ii) spraying the solvent into the gas stream and (iii) countercurrent contact between the gas stream flowing upward and the solvent flowing downward in a tray or packed column. In all three variants, apparatus known to those skilled in the art may be used for gas absorption. When choosing the solvent to be used, care must be taken that it does not react with the reactant, for example the preferably used MA. Useful solvents are: tricresyl phosphate, dibutyl maleate, butyl maleate, high molecular weight waxes, aromatic hydrocarbons having a molecular weight of from 150 to 400 and a boiling point above 140° C., for example dibenzylbenzene, alkyl phthalates and dialkyl phthalates having $C_1$–$C_{18}$-alkyl groups, for example dimethyl phthalate, diethyl phthalate, dibutyl phthalate, di-n-propyl and diisopropyl phthalate, undecyl phthalate, diundecyl phthalate, methyl phthalate, ethyl phthalate, butyl phthalate, n-propyl or isopropyl phthalate; di-$C_1$–$C_4$-alkyl esters of other aromatic and aliphatic dicarboxylic acids, for example dimethyl 2,3-naphthalenedicarboxylate, dimethyl 1,4-cyclohexanedicarboxylate; $C_1$–$C_4$-alkyl esters of other aromatic and aliphatic dicarboxylic acids, for example methyl 2,3-naphthalenedicarboxylate, methyl 1,4-cyclohexanedicarboxylate; methyl esters of long-chain fatty acids having for example from 14 to 30 carbon atoms, high-boiling ethers, for example dimethyl ethers of polyethylene glycol, for example tetraethylene glycol dimethyl ether. Preference is given to the use of phthalates.

The solution resulting from treatment with the absorbent generally has an MA content of from about 5 to 400 grams per liter.

The gas stream remaining after treatment with the absorbent contains mainly the by-products of the preceding partial oxidation such as water, carbon monoxide, carbon dioxide, unconverted butanes, acetic acid and acrylic acid. The offgas stream is virtually free of MA.

The dissolved MA is then stripped from the absorbent. This is effected using hydrogen at or at a maximum of 10% above the pressure of the subsequent hydrogenation or alternatively under reduced pressure with subsequent condensation of remaining MA. In the stripping column, a temperature profile is observed which results from the boiling points of MA at the top and the virtually MA-free absorbent at the bottom of the column at the column pressure in each case and the dilution with carrier gas (in the first case with hydrogen) used.

In order to avoid solvent losses, rectifying internals may be disposed above the feed of the crude MA stream. The virtually MA-free absorbent taken off at the bottom is fed back into the absorption zone. The $H_2$/MA ratio is from about 20 to 600. Otherwise, the condensed MA is pumped into an evaporator and evaporated there into the cycle gas stream.

The MA-hydrogen stream also contains by-products which result from the partial oxidation of n-butane, butenes or benzene using oxygen-containing gases, and also unremoved absorbent. The by-products are in particular acetic acid and acrylic acid, and there is also water, maleic acid and also dialkyl phthalates which are preferably used as absorbents. The MA contains acetic acid in quantities from 0.01 to 1% by weight, preferably from 0.1 to 0.8% by weight, and acrylic acid in quantities from 0.01 to 1% by weight, preferably from 0.1 to 0.8% by weight, based on MA. In the hydrogenation stage, acetic acid and acrylic acid are partially or completely hydrogenated to ethanol and propanol respectively. The maleic acid content is from 0.01 to 1% by weight, in particular from 0.05 to 0.3% by weight, based on MA.

When dialkyl phthalates are used as absorbents, the content thereof in the MA depends strongly on the correct operation of the stripping column, in particular of the rectifying section. Phthalate contents of up to 1.0% by weight, in particular of up to 0.5% by weight, should not be exceeded when the column is operated in a suitable manner, since the consumption of absorbents otherwise becomes too high.

The hydrogen/maleic anhydride stream which is preferably obtained as described above is then fed into the first hydrogenation reactor or the first hydrogenation zone of a reactor and hydrogenated. The catalyst activities and on-stream times are virtually unchanged compared to the use of extensively, for example by distillation, prepurified MA.

The gas stream leaving the first reactor or the first hydrogenation zone of a reactor is fed with any recycled GBL to the second hydrogenation.

The recycled gas of the second stage can be recycled into the entrance of the first stage.

In all reaction variants, the gas stream leaving the second reactor may be cooled, preferably to from 10 to 60° C. The reaction products are condensed out and passed into a separator. The uncondensed gas stream may be taken from the separator and fed into the cycle gas compressor. By-products formed in the recycled gas stream may be removed by measures known to those skilled in the art, preferably by bleeding off a small quantity of cycle gas. The reaction products which have condensed out are withdrawn from the system and fed to a workup. The coupling products and by-products in the liquid phase which has condensed out are mainly THF and n-butanol, as well as small quantities of propanol.

The by-products and also water and the desired product BDO are then isolated from the liquid hydrogenation residue of the second stage. This is generally effected by fractional distillation. By-products and intermediates, for example GBL and di-BDO, may be returned to the hydrogenation of the first and/or second stage, preferably of the second stage, or alternatively worked up distillatively.

The process according to the invention may be carried out batchwise, semicontinuously or continuously. Preference is given to carrying it out continuously.

An important parameter is the maintenance of a suitable reaction temperature in both hydrogenation stages.

In the first hydrogenation stage, preference is given to obtaining this by a sufficiently high temperature of the reactants when entering the first hydrogenation reactor or the first reaction zone of a reactor. This starting hydrogenation temperature is from 200 to 300° C., preferably from 235 to 270° C. In order to obtain the desired selectivity and yield in the first stage, the reaction should preferably be carried out in such a manner that the catalyst bed where the actual reaction takes place is at a suitably high reaction temperature. This hot spot temperature is set after the reactants enter the reactor and is preferably from 210 to 310° C., in particular from 245 to 280° C. Preference is given to carrying out the process in such a manner that the entrance temperature and the exit temperature of the reaction gases are below this hot spot temperature. The hot spot temperature is advantageously in the first half of the reactor, in particular when it is a tube bundle reactor. The hot spot temperature is preferably from 5 to 30° C., in particular from 5 to 15° C., more preferably from 5 to 10° C., above the entrance temperature. When the hydrogenation is carried out below the minimum entrance and hot spot temperatures and MA is used as the reactant, the quantity of SA generally increases while at the same time the GBL and BDO quantities decrease. Such a temperature also results in the observation of catalyst deactivation in the course of the hydrogenation due to fouling by succinic acid, fumaric acid and/or SA and mechanical damage to the catalyst. In contrast, when MA is used as the reactant above the maximum entrance and hot spot temperatures, the BDO yield and selectivity generally fall to unsatisfactory values. Increased formation of THF, n-butanol and n-butane is observed, i. e. the products of further hydrogenation.

The entrance temperature (starting hydrogenation temperature) into the second reactor is generally equal to the entrance temperature into the first reactor or less, and preference is given to a lower entrance temperature into the second reactor than the entrance temperature into the first reactor.

In the second hydrogenation stage, the entrance temperature (starting hydrogenation temperature) is from 140° C. to 260° C., preferably from 160° C. to 225° C., in particular from 180 to 200° C. When the hydrogenation is carried out below the minimum entrance temperature, the quantity of BDO formed falls. The catalyst loses activity. Below the minimum temperature, condensation of the starting materials and damage to the copper catalyst by water are also to be expected. In contrast, when GBL is used as the reactant for hydrogenation above the maximum entrance temperature, the BDO yield and selectivity fall to unsatisfactory values. At these temperatures the hydrogenation equilibrium between BDO and GBL is on the side of GBL so that less conversion is obtained, but increased by-product formation by overhydrogenation to THF, n-butanol and n-butane is observed at relatively high temperatures.

The starting hydrogenation temperature may be the same in both hydrogenation stages. The starting hydrogenation temperature in the second hydrogenation stage is preferably less than in the first hydrogenation stage.

The temperature increase of the gas stream in the reactor should not exceed 110° C., preferably 40° C., and in particular should not be more than 20° C. Large temperature increases here also lead to overhydrogenation reactions and (BDO+GBL) selectivity loss.

In both the first hydrogenation stage and the second hydrogenation stage, the pressure is from 10 to 100 bar, preferably from 15 to 50 bar and more preferably a pressure of from 20 to 40 bar is selected. In this pressure range, the hydrogenation of MA proceeds with very substantial suppression of THF formation from the initially formed intermediate GBL. At the temperature specified for the second hydrogenation stage, the conversion of GBL to BDO is high and the THF formation is low. These effects are obvious in particular when a low hydrogenation temperature is specified in the second hydrogenation stage than in the first hydrogenation stage.

The catalyst hourly space velocity of the first hydrogenation stage is preferably in the range from 0.02 to 1, in particular from 0.05 to 0.5, kg of reactant/l of catalyst·hour. In the case of MA, when the catalyst hourly space velocity of the first stage increases above this range, an increase of the SA and succinic acid contents in the hydrogenation effluent is observed. The catalyst hourly space velocity of the second hydrogenation stage is in the range from 0.02 to 1.5, in particular from 0.1 to 1, kg of reactant/l of catalyst·hour. When the catalyst hourly space velocity is increased above this range, incomplete conversion of GBL is to be expected. This may optionally be compensated for by an increased recycling rate, although it will be appreciated that this is not preferred.

The hydrogen/reactant molar ratio is also a parameter which influences the product distribution and also the economic viability of the process according to the invention. From an economic point of view, a low hydrogen/reactant ratio is desirable. The lower limit is at a value of 5, although higher hydrogen/reactant molar ratios of from 20 to 600, preferably from 40 to 400 and in particular from 60 to 350 are generally used.

In order to attain the hydrogen/reactant molar ratios used according to the invention, a portion, advantageously the majority, of the hydrogen is customarily recycled in both the first and the second hydrogenation stages. To this end, the cycle gas compressor familiar to those skilled in the art is generally used. An advantage of the present invention is that only one hydrogenation cycle has to be constructed and only one compressor has to be provided to carry out two hydrogenation stages.

The hydrogen quantity consumed by hydrogenation is replaced. In a preferred embodiment, a portion of the cycle gas is bled off, in order to remove inert compounds, for example n-butane. The recycled hydrogen may also, optionally after preheating, be utilized to evaporate the reactant stream.

Together with the hydrogen cycle gas, all products are recycled which do not condense out or do so incompletely when the gas streams leaving the hydrogenation reaction are cooled. These are in particular THF, water and by-products such as methane and butane. The cooling temperature is preferably from 0 to 60° C., preferably from 20 to 45° C.

Useful reactor types include all apparatus suitable for heterogeneously catalyzed reactions having gaseous reaction and product streams. Preference is given to tubular reactors, shaft reactors or reactors having internal heat removal means, for example tube bundle reactors, and the use of a fluidized bed is also possible. Particular preference is given to using tube bundle reactors for the first hydrogenation stage, and to shaft reactors for the second hydrogenation stage. In both the first and the second hydrogenation stage, more than one reactor connected in parallel or in series may be used. In principle, there may also be intermediate feeding between the catalyst beds. It is also possible to provide intermediate cooling between or in the catalyst beds. When fixed bed reactors are used, dilution of the catalyst by inert material is possible. The process according to the invention is most preferably carried out in a two-zone reactor.

An important point of the present invention is the choice of the catalysts for both stages which have copper oxide as the catalytically active main component. This is applied to an oxidic support which may have a small number of acidic sites. When a catalyst having too high a number of acidic sites is used, BDO is dehydrated and THF is formed.

A suitable support material which has a sufficiently low number of acidic sites is a material selected from the group of ZnO, $Al_2O_3$, $SiO_2$, $TiO_2$, $ZrO_2$, $CeO_2$, MgO, CaO, SrO, BaO and $Mn_2O_3$ and mixtures thereof. Preferred support materials are ZnO/$Al_2O_3$ mixtures, the delta-, theta-, alpha- and eta-modifications of $Al_2O_3$ and also mixtures which comprise at least one component each firstly from the group of $SiO_2$, $TiO_2$, $ZrO_2$, and secondly from the group of ZnO, MgO, CaO, SrO and BaO. Particularly preferred support materials are pure ZnO, ZnO/$Al_2O_3$ mixtures in a weight ratio of from 100:1 to 1:2 and mixtures of $SiO_2$ with MgO, CaO and/or ZnO in a weight ratio of 200:1 to 1:1.

The copper oxide quantity is $\leq 95\%$ by weight, preferably from 5 to 95% by weight, in particular from 15 to 80% by weight; the support is used in quantities of $\geq 5\%$ by weight, preferably from 5 to 95% by weight, in particular from 20 to 85% by weight.

Owing to the toxicity of chromium catalysts, preference is giving to using chromium-free catalysts. It will be appreciated that corresponding chromium catalysts known to those skilled in the art are technically also suitable for use in the process according to the invention, although the desired advantages which are in particular of environmental and technical nature do not accrue.

The same catalyst may be used in both hydrogenation stages, but preference is given to the use of different catalysts.

Optionally, the catalysts used according to the invention may comprise one or more further metals or a compound thereof, preferably an oxide, from groups 1 to 14 (IA to VIIIA and IB to IVB of IUPAC nomenclature) of the Periodic Table. When a further metal is used, preference is given to using Pd in quantities of $\leq 1\%$ by weight, preferably $\leq 0.5\%$ by weight, in particular $\leq 0.2\%$ by weight. However, the use of a further metal or metal oxide is not preferred.

The catalysts used may additionally contain an auxiliary in a quantity of from 0 to 10% by weight. Auxiliaries are organic and inorganic materials which contribute to improved processing during catalyst preparation and/or to an increase in the mechanical stability of the catalyst shaped bodies. Useful auxiliaries are known to those skilled in the art; examples include graphite, stearic acid, silica gel and copper powder.

The catalysts can be prepared by methods known to those skilled in the art. Preference is given to processes which provide the copper oxide finely divided and intimately mixed with the other components, greater preference to impregnation and precipitation reactions.

These starting materials may be processed by known methods to give the shaped bodies, for example extrusion, tableting or agglomeration processes, optionally with the use of auxiliaries.

Alternatively, catalysts according to the invention may be prepared, for example, by applying the active component to a support, for example by coating or vapor deposition. Catalysts according to the invention may also be obtained by shaping a heterogeneous mixture of active component or precursor compound thereof with a support component or precursor compound thereof.

The hydrogenation according to the invention which may, as well as MA, use other, above-defined $C_4$-dicarboxylic acids or derivatives thereof as reactants uses the catalyst in reduced, activated form. The catalyst is activated using reducing gases, preferably hydrogen or hydrogen/inert gas mixtures either before or after installation in the reactors where the process according to the invention is carried out. If the catalyst has been installed in oxidic form in the reactor, it may be activated either before startup of the plant with the hydrogenation according to the invention or else during the startup, i. e. in situ. Separate activation before plant startup is generally effected using reducing gases, preferably hydrogen or hydrogen/inert gas mixtures at elevated temperatures, preferably from 100 to 350° C. In situ activation is effected when starting up the plant by contacting with hydrogen at elevated temperature.

Preference is given to using the catalysts in the form of shaped bodies. Examples include extrudates, ribbed extrudates, other extrudate forms, tablets, rings, spheres and spall.

The BET surface area of the copper catalysts in the oxidic state should be from 10 to 300 m$^2$/g, preferably from 15 to 175 m$^2$/g, in particular from 20 to 150 m$^2$/g. The copper surface area (N$_2$O decomposition) of the reduced catalyst in the installed state should be >0.2 m$^2$/g, preferably >1 m$^2$/g, in particular >2 m$^2$/g.

In one variant of the invention, catalysts are used which have a defined porosity. The shaped bodies of these catalysts have a pore volume of ≧0.01 ml/g for pore diameters of >50 nm, preferably of ≧0.025 ml/g for pore diameters of >100 nm and in particular of ≧0.05 ml/g for pore diameters of >200 nm. The ratio of macropores having a diameter of >50 nm to the total pore volume for pores having a diameter of >4 nm is also >10%, preferably >20%, in particular >30%. The porosities mentioned were determined by mercury intrusion according to DIN 66133. The data were evaluated in the pore diameter range of from 4 nm to 300 µm.

The catalysts used according to the invention generally have sufficient on-stream time. However, in the event that the activity and/or selectivity of the catalyst should fall in the course of its operating time, it may be regenerated by methods known to those skilled in the art. These include preferably reductive treatment of the catalyst in a hydrogen stream at elevated temperature. The reductive treatment may optionally be followed by oxidative treatment. To this end, a molecular oxygen-containing gas mixture, for example air, is passed through the catalyst bed at elevated temperature. There is also the possibility of washing the catalysts with a suitable solvent, for example ethanol, THF, BDO or GBL, and then drying them in a gas stream.

The process according to the invention allows selectivities for butanediol to be achieved which are generally slightly lower than the selectivities obtained by the process according to our own application "Two-stage process for preparing butanediol in two reactors" of Jun. 11, 2002 and in which only very small amounts of THF are formed. In contrast, the process according to the present application always provides an obvious amount of THF which, when process operation is optimized, is a few % by weight. When process operation is not optimized, for example when the same temperatures are applied and identical catalysts are used in both hydrogenation stages, up to 50% by weight of THF (based on BDO) is obtained. However, the increased formation of THF, which has to be removed from the desired product of value BDO, is compensated for by the low apparatus demands in carrying out the process according to the present application.

We claim:

1. A process for preparing optionally alkyl-substituted 1,4-butanediol by two-stage catalytic hydrogenation in the gas phase of C$_4$-dicarboxylic acids and/or of derivatives thereof having the following steps:
   a) introducing a gas stream of a C$_4$-dicarboxylic acid or of a derivative thereof at from 200 to 300° C. and from 10 to 100 bar into a first reactor or into a first reaction zone of a reactor and catalytically hydrogenating it in the gas phase to a product which contains mainly optionally alkyl-substituted γ-butyrolactone;
   b) introducing the product stream obtained in this way into a second reactor or into a second reaction zone of a reactor at a temperature of from 140° C. to 260° C. and catalytically hydrogenating it in the gas phase to optionally alkyl-substituted 1,4-butanediol;
   steps a) and b) being carried out at the same pressure;
   c) removing the desired product from intermediates, by-products and any unconverted reactant;
   d) optionally recycling unconverted intermediates into one or both hydrogenation states,
   said hydrogenation stages each using a catalyst which comprises ≦95% by weight of CuO, and ≧5%, of an oxidic support, and the product mixture removed from the first hydrogenation stage being introduced without further purification into the second hydrogenation stage.

2. The process as claimed in claim 1, wherein the entrance temperature into the second reactor or into the second reaction zone of a reactor is lower than the entrance temperature into the first reactor or into the first reaction zone.

3. The process as claimed in claim 1, wherein the entrance temperature into the first reactor is from 235 to 270° C. and the entrance temperature into the second reactor is from 160° C. to 225° C., in particular from 180 to 200° C.

4. The process as claimed in claim 1, wherein the hot spot temperature in the first reactor is from 210 to 310° C., and the process is carried out in such a manner that the hot spot temperature is above the entrance temperature and the exit temperature of the reaction gases, and is from 5 to 30° C., above the entrance temperature.

5. The process as claimed in claim 1, wherein the pressure in both the first hydrogenation stage and the second hydrogenation stage is from 10 to 100 bar.

6. The process as claimed in claim 1, wherein the catalyst hourly space velocity of the first hydrogenation stage is in the range from 0.02 to 1, kg of reactant/l catalyst·hour, and the catalyst hourly space velocity of the second hydrogenation stage is in the range form 0.02 to 1.5, kg of reactant/l of catalyst·hour.

7. The process as claimed in claim 1, wherein the hydrogen/reactant molar ratio in both reaction stages is ≧5.

8. A process as claimed in claim 7, wherein the hydrogen/reactant ratio in the first stage hydrogenation is from 20 to 200.

9. The process as claimed in claim 1, wherein the reactors used are selected from the group consisting of tubular reactors, shaft reactors, reactors having internal heat removal means, preferably tube bundle reactors and fluidized bed reactor.

10. The process as claimed in claim 9, wherein a tube bundle reactor is used in the first hydrogenation stage.

11. The process as claimed in claim 9, wherein a shaft reactor is used in the second hydrogenation stage.

12. The process as claimed in claim 1, wherein more than one rector connected in parallel or in series is used in the first and/or second hydrogenation stage.

13. The process as claimed in claim 1, wherein a two-zone reactor is used.

14. The process as claimed in claim 1, wherein the process is carried out in an apparatus having a hydrogenation cycle and a compressor.

15. The process as claimed in claim 1, wherein the support material of the catalyst is selected from the group of ZnO, Al$_2$O$_3$, SiO$_2$, TiO$_2$, ZrO$_2$, CeO$_2$, MgO, CaO, SrO, BaO and Mn$_2$O$_3$ and mixtures thereof, preferably from the group of ZnO/Al$_2$O$_3$ mixtures, the delta-, theta-, alpha- and eta-modifications of Al$_2$O$_3$ and also mixtures which comprise at least one component each firstly from the group of SiO$_2$, TiO$_2$, ZrO$_2$, and secondly from the group of ZnO, MgO, CaO, SrO and BaO.

16. The process as claimed in claim 1, wherein the support material is selected from ZnO, ZnO/Al$_2$O$_3$ mixtures in a weight ratio of from 100:1 to 1:2 and mixtures SiO$_2$ with MgO, CaO and/or ZnO in a weight ratio of 200:1 to 1:1.

17. The process as claimed in claim 1, wherein the catalyst comprises one or more further metals from groups 1 to 14 of the Periodic Table.

18. The process as claimed in claim 1, wherein BET surface area of the copper catalysts in the oxidic state is from 10 to 300 m$^2$g.

19. The process as claimed in claim 1, wherein the copper surface area of the reduced catalyst in the installed state is >0.2 m$^2$g.

20. The process as claimed in claim 1, wherein the catalysts used in the first and second reactors are identical or different, preferably different.

21. The process as claimed in claim 1, wherein the shaped bodies of the catalyst used have a pore volume of $\geq$0.01 ml/g for pore diameter of >50 nm.

22. The process as claimed in claim 1, wherein the shaped bodies of the catalyst used have a ratio of micropores having a diameter of >50 nm to the total pore volume for pores having a diameter of >4 nm of >10%.

23. The process as claimed in claim 1, wherein the reactant used in the reaction is maleic anhydride.

24. The process as claimed in claim 1, wherein maleic anhydride is used which has been prepared by oxidizing benzene, $C_4$-olefins or n-butane, and the crude maleic anhydride obtained by oxidation has been extracted from the crude product mixture using a solvent (absorbent) and then stripped from this solvent using hydrogen.

25. A process as claimed in claim 1, wherein the absorbent is selected from the group consisting of tricresyl phosphate, dibutyl maleate, high molecular weight waxes, aromatic hydrocarbons having a molecular weight of from 150 to 400 and boiling point above 140° C., di-$C_1$–$C_4$-alkyl esters of aromatic and aliphatic dicarboxylic acids, methyl esters of long-chain fatty acids having from 14 to 30 carbon atoms, high-boiling ethers, and alkyl phthalates and dialkyl phthalates having $C_1$–$C_{18}$-alkyl groups.

26. The process as claimed in claim 1, wherein the maleic anhydride is stripped from the absorbent under reduced pressure of pressures which correspond to the hydrogenation pressure or are a maximum of 10% above this pressure.

27. The process as claimed in claim 1, which is carried out batchwise, semicontinuously or continuously, preferably continuously.

28. The process as claimed in claim 1, wherein the catalyst is used in the form of shaped bodies, preferably in the form of extudates, ribbed extrudates, tablets, rings, shperes or spall.

* * * * *